US009833495B2

(12) United States Patent
Rosenkilde Kjær et al.

(10) Patent No.: US 9,833,495 B2
(45) Date of Patent: *Dec. 5, 2017

(54) ORAL TREATMENT OF INFLAMMATORY BOWEL DISEASE

(71) Applicant: Defensin Therapeutics ApS, Gentofte (DK)

(72) Inventors: Tanja Maria Rosenkilde Kjær, Holte (DK); Birgitte Andersen, Bagsværd (DK); Karoline Sidelmann Brinch, København NV (DK)

(73) Assignee: Defensin Therapeutics ApS, Gentofte (DK)

( * ) Notice: Subject to any disclaimer, the term of this patent is extended or adjusted under 35 U.S.C. 154(b) by 0 days.

This patent is subject to a terminal disclaimer.

(21) Appl. No.: 14/942,307

(22) Filed: Nov. 16, 2015

(65) Prior Publication Data

US 2016/0129081 A1    May 12, 2016

Related U.S. Application Data

(63) Continuation of application No. 14/131,364, filed as application No. PCT/EP2012/063137 on Jul. 5, 2012, now Pat. No. 9,217,021.

(60) Provisional application No. 61/506,437, filed on Jul. 11, 2011.

(30) Foreign Application Priority Data

Jul. 8, 2011  (EP) .................................. 11173351

(51) Int. Cl.
| A61K 38/17 | (2006.01) |
| A61K 9/00 | (2006.01) |
| C07K 14/00 | (2006.01) |
| C07K 14/47 | (2006.01) |

(52) U.S. Cl.
CPC ........ *A61K 38/1729* (2013.01); *A61K 9/0053* (2013.01); *C07K 14/4723* (2013.01)

(58) Field of Classification Search
CPC .. A61K 38/1729; A61K 9/0053; A61K 38/17; A61K 9/00; C07K 14/4723
USPC .................................................. 514/1.1, 21.3
See application file for complete search history.

(56) References Cited

U.S. PATENT DOCUMENTS

| 5,223,409 | A | 6/1993 | Ladner et al. |
| 7,338,936 | B2 | 3/2008 | Lim et al. |
| 7,384,911 | B2 | 6/2008 | Bulet et al. |
| 7,862,826 | B2 | 1/2011 | Murphy et al. |
| 8,232,242 | B2 | 7/2012 | Kjaer et al. |
| 8,232,248 | B2 | 7/2012 | Kjaer et al. |
| 8,802,621 | B2 | 8/2014 | Kjaer et al. |
| 9,217,021 | B2 | 12/2015 | Kjaer et al. |
| 9,279,010 | B2 | 3/2016 | Kjaer et al. |
| 2006/0115480 | A1 | 6/2006 | Hillman |
| 2008/0194481 | A1 | 8/2008 | Rosen et al. |
| 2010/0016230 | A1 | 1/2010 | Kjaer et al. |
| 2010/0016231 | A1 | 1/2010 | Kjaer et al. |
| 2010/0016232 | A1 | 1/2010 | Kjaer et al. |
| 2011/0251139 | A1 | 10/2011 | Kjaer et al. |
| 2012/0244102 | A1 | 9/2012 | Hashimoto et al. |
| 2012/0309678 | A1 | 12/2012 | Kjaer et al. |
| 2012/0309686 | A1 | 12/2012 | Kjaer et al. |
| 2013/0052213 | A1 | 2/2013 | Kjaer et al. |
| 2013/0172235 | A1 | 7/2013 | Kjaer et al. |
| 2014/0135258 | A1 | 5/2014 | Kjaer et al. |
| 2014/0213521 | A1 | 7/2014 | Kjaer et al. |

FOREIGN PATENT DOCUMENTS

| EP | 08160761.6 | 7/2008 |
| EP | 2 343 292 A1 | 7/2011 |
| JP | 2011121887 A | 6/2011 |
| WO | WO 92/06204 A1 | 4/1992 |
| WO | WO 95/17413 A1 | 6/1995 |
| WO | WO 95/22625 A1 | 8/1995 |
| WO | WO 01/38349 A2 | 5/2001 |
| WO | WO 2007/007116 A1 | 1/2007 |
| WO | WO 2007/081486 A2 | 7/2007 |
| WO | WO 2007/087557 A2 | 8/2007 |
| WO | WO 2009/033776 A1 | 3/2009 |
| WO | WO 2010/007165 A2 | 1/2010 |
| WO | WO 2010/007166 A2 | 1/2010 |
| WO | WO 2010/007168 A2 | 1/2010 |
| WO | WO 2010/029925 A1 | 3/2010 |
| WO | WO 2013/007596 A2 | 1/2013 |

OTHER PUBLICATIONS

Final Office Action from U.S. Appl. No. 12/504,909, titled: "Treatment of Inflammatory Bowel Diseases With Mammal Beta Defensins," dated Aug. 25, 2011.
Final Office Action from U.S. Appl. No. 12/504,920, titled: "Treatment of Rheumatoid Arthritis With Mammal Beta Defensins," dated Aug. 25, 2011.
Final Office Action from U.S. Appl. No. 13/158,638, titled: "Treatment of Inflammatory Bowel Diseases With Mammal Beta Defensins," dated Nov. 14, 2012.
Notice of Abandonment from U.S. Appl. No. 12/504,930, titled: "Treatment of Inflammatory Diseases With Mammal Beta Defensins," dated Jan. 28, 2013.
Notice of Abandonment from U.S. Appl. No. 13/542,747, "Oral Treatment of Inflammatory Bowel Disease," dated Mar. 18, 2014.
Notice of Abandonment from U.S. Appl. No. 13/544,237, titled: "Treatment of Rheumatoid Arthritis With Mammal Beta Defensins," dated Aug. 30, 2013.

(Continued)

*Primary Examiner* — Julie Ha
(74) *Attorney, Agent, or Firm* — Hamilton, Brook, Smith & Reynolds, P.C.

(57) ABSTRACT

Treatment of an inflammatory bowel disease in a subject in need thereof by simultaneous or successive parenteral and oral administration of a mammalian beta defensin is described. Oral administration of mammalian beta defensin to a subject during remission to keep said subject suffering from IBD in remission, prolong remission in said subject suffering from IBD, to reduce the occurrence of relapse in said subject suffering from IBD, or any combination thereof, is also described.

9 Claims, 3 Drawing Sheets

(56) References Cited

OTHER PUBLICATIONS

Notice of Abandonment from U.S. Appl. No. 13/544,253, titled: "Treatment of Inflammatory Bowel Diseases With Mammal Beta Defensins," dated May 30, 2013.
Notice of Allowance from U.S. Appl. No. 12/504,909, titled: "Treatment of Inflammatory Bowel Diseases With Mammal Beta Defensins," dated Apr. 4, 2012.
Notice of Allowance from U.S. Appl. No. 12/504,920, titled: "Treatment of Rheumatoid Arthritis With Mammal Beta Defensins," dated Mar. 29, 2012.
Notice of Allowance from U.S. Appl. No. 12/504,930, titled: "Treatment of Inflammatory Diseases With Mammal Beta Defensins," dated Oct. 15, 2012.
Office Action from U.S. Appl. No. 13/158,638, titled: "Treatment of Inflammatory Bowel Diseases With Mammal Beta Defensins," dated Jun. 26, 2012.
Office Action from U.S. Appl. No. 12/504,909, titled: "Treatment of Inflammatory Bowel Diseases With Mammal Beta Defensins," dated Mar. 28, 2011.
Office Action from U.S. Appl. No. 12/504,920, titled: "Treatment of Rheumatoid Arthritis With Mammal Beta Defensins," dated Apr. 1, 2011.
Office Action from U.S. Appl. No. 12/504,930, titled: "Treatment of Inflammatory Diseases With Mammal Beta Defensins," dated Aug. 25, 2011.
Office Action from U.S. Appl. No. 12/504,930, titled: "Treatment of Inflammatory Diseases With Mammal Beta Defensins," dated May 1, 2012.
Office Action from U.S. Appl. No. 13/158,638, titled: "Treatment of Inflammatory Bowel Diseases With Mammal Beta Defensins," dated Jan. 17, 2012.
Office Action from U.S. Appl. No. 13/158,638, titled: "Treatment of Inflammatory Bowel Diseases With Mammal Beta Defensins," dated Mar. 10, 2014.
Office Action from U.S. Appl. No. 13/544,253, titled: "Treatment of Inflammatory Bowel Diseases With Mammal Beta Defensins," dated Nov. 1, 2012.
Office Action from U.S. Appl. No. 13/588,343, titled: "Novel Immunomodulatory Peptide," dated Oct. 31, 2013.
Reply from U.S. Appl. No. 12/504,909, titled: "Treatment of Inflammatory Bowel Diseases With Mammal Beta Defensins," filed Jul. 28, 2011.
Reply from U.S. Appl. No. 12/504,909, titled: "Treatment of Inflammatory Bowel Diseases With Mammal Beta Defensins," filed Dec. 22, 2011.
Reply from U.S. Appl. No. 12/504,920, titled: "Treatment of Rheumatoid Arthritis With Mammal Beta Defensins," filed Jul. 28, 2011.
Reply from U.S. Appl. No. 12/504,920, titled: "Treatment of Rheumatoid Arthritis With Mammal Beta Defensins," filed Dec. 22, 2011.
Reply from U.S. Appl. No. 12/504,930, titled: "Treatment of Inflammatory Diseases With Mammal Beta Defensins," filed Dec. 22, 2011.
Reply from U.S. Appl. No. 12/504,930, titled: "Treatment of Inflammatory Diseases With Mammal Beta Defensins," filed Jul. 27, 2012.
Reply from U.S. Appl. No. 13/158,638, titled: "Treatment of Inflammatory Bowel Diseases With Mammal Beta Defensin," filed Apr. 17, 2012.
Reply from U.S. Appl. No. 13/158,638, titled: "Treatment of Inflammatory Bowel Diseases With Mammal Beta Defensins," filed Sep. 19, 2012.
Reply from U.S. Appl. No. 13/158,638, titled: "Treatment of Inflammatory Bowel Diseases With Mammal Beta Defensins," filed Jan. 30, 2014.
Aldhous, M. C., et al., "Dysregulation of Human β-Defensin-2 Protein in Inflammatory Bowel Disease," PLoS ONE, 4(7): e6285 (2009).
Asadullah, K., et al., "IL-10 is a Key Cytokine in Psoriasis: Proof of Principle by IL-10 Therapy: A New Therapeutic Approach," J. Clin. Invest., 101(4): 783-794 (1998).
Berg, D. J., et al., "Enterocolitis and Colon Cancer in Interleukin-10-deficient Mice Are Associated with Aberrant Cytokine Production and CD4+ Th1-like Responses," J. Clin. Invest., 98(4): 1010-1020. (1996).
Bhavsar, M. D., and Amiji, M. M., "Oral IL-10 gene delivery in a microsphere-based formulation for local transfection and therapeutic efficacy in inflammatory bowel disease," Gene Therapy, 15: 1200-1209 (2008).
Boniotto, M., et al., "Human β-Defensin 2 Induces a Vigorous Cytokine Response in Peripheral Blook Mononuclear Cells," Antimicrobial Agents and Chemotherapy, 50(4): 1433-1441 (2006).
Bowdish, D. M. E., et al., "Immunomodulatory Properties of Defensins and Cathelicidins," CTMI, 306: 27-66 (2006).
Bowie, J. U., and Sauer, R. T., "Identifying determinants of folding and activity for a protein of unknown structure," Proc. Natl. Acad. Sci. USA, 86: 2152-2156 (1989).
Chronnell, C. M. T., et. al., "Human β Defensin-1 and -2 Expression in Human Pilosebaceous Units: Upregulation in Acne Vulgaris Lesions," J. Invest. Dermatol., 117: 1120-1125 (2001).
Cobo, Eduardo R. and Chadee, Kris, "Antimicrobial Human β-Defensins in the Colon and Their Role in Infectious and Non-Infectious Diseases", Pathogens, 2, 177-192, 2013.
Crohn Disease from Merck Manual, pp. 1-4. Accessed Apr. 1, 2015.
Cunningham, B. C., and Wells, J. A., "High-Resolution Epitope Mapping of hGH-Receptor Interactions by Alanine-Scanning Mutagenesis," Science, 244(4908): 1081-1085 (1989).
de Jongh, G. J., et al., "High Expression Levels of Keratinocyte Antimicrobial Proteins in Psoriasis Compared with Atopic Dermatitis," J. Invest. Dermatol., 125: 1163-1173 (2005).
Derbyshire, K. M., et al., "A simple and efficient procedure for saturation mutagenesis using mixed oligodeoxynucleotides," Gene, 46: 145-152 (1986).
Donnarumma, G., et al., "Anti-inflammatory effects of moxifloxacin and human β-defensin 2 association in human lung epithelial cell line (A549) stimulated with lipopolysaccharide," Peptides, 28: 2286-2292 (2007).
Duvallet E., et al., "Interleukin-23: A key cytokine in inflammatory diseases," Annals of Medicine, 43: 503-511 (2011).
Fahlgren, A., et al., "Increased expression of antimicrobial peptides and lysozyme in colonic epithelial cells of patients with ulcerative colitis," Clin. Exp. Immunol., 131: 90-101 (2003).
Fedorak, R. N., et al., "Recombinant Human Interleukin 10 in the Treatment of Patients With Mild to Moderately Active Crohn's Disease," Gastroenterology, 119: 1473-1482 (2000).
Feldmann, M., and Maini, R. N., "TNF defined as a therapeutic target for rheumatoid arthritis and other autoimmune diseases," Nature Medicine, 9(10): 1245-1250 (2003).
Fellowes, R., et al., "Amelioration of established collagen induced arthritis by systemic IL-10 gene delivery," Gene Therapy, 7: 967-977 (2000).
Finnegan, A., et al., "Collagen-induced arthritis is exacerbated in IL-10-deficient mice," Arthritis Res. Ther., 5(1): R18-R24 (2003).
Finnegan, A., et al., "Proteoglycan (Aggrecan)-Induced Arthritis in BALB/c Mice Is a Th1-Type Disease Regulated by Th2 Cytokines," J. Immunol., 163: 5383-5390 (1999).
Gambichler, T., et al., "Expression of human β-defensins in patients with mycosis fungoides," Arch. Dermatol. Res., 299: 221-224 (2007).
Gersemann, M., et al., "Crohn's disease-Defect in innate defence," World J. Gastroenterol., 14(36): 5499-5503 (2008).
Hilton, D. J., et al., "Saturation Mutagenesis of the WSXWS Motif of the Erythropoietin Receptor," The Journal of Biological Chemistry, 271(9):4699-4708 (1996).
International Preliminary Report on Patentability, International Application No. PCT/EP2012/063137 titled: "Oral Treatment of Inflammatory Bowel Disease", dated Jan. 14, 2014.
International Search Report for International Application No. PCT/EP2012/063137 titled: "Oral Treatment of Inflammatory Bowel Disease", dated Feb. 11, 2013.

(56) References Cited

OTHER PUBLICATIONS

Jansen, P. A. M., et al., "β-Defensin-2 Protein Is a Serum Biomarker for Disease Activity in Psoriasis and Reaches Biologically Relevant Concentrations in Lesional Skin," PLoS ONE, 4(3): e4725 (2009).
Kapel, N., et al., "Fecal β-Defensin-2 in Children With Inflammatory Bowel Diseases," Journal of Pediatric Gastroenterology and Nutrition, 48: 117-120 (2008).
Kasama, T., et al., "Interleukin-10 Expression and Chemokine Regulation During the Evolution of Murine Type II Collagen-induced Arthritis," J. Clin. Invest., 95: 2868-2876 (1995).
Kawada, M., et al., "Insights from advances in research of chemically induced experimental models of human inflammatory bowel disease," World J. Gastroenterol., 13(42): 5581-5593 (2007).
Lehrer, R.I., "Primate Defensins," Nature Reviews Microbiology, 2: 727-738 (2004).
Lindsay, J. O., et al., "Local delivery of adenoviral vectors encoding murine interleukin 10 induces colonic interleukin 10 production and is therapeutic for murine colitis," Gut, 52: 363-369 (2003).
Lowman, H. B., et al., "Selecting High-Affinity Binding Proteins by Monovalent Phage Display," Biochemistry, 30: 10832-10838 (1991).
Maini, R. N., et al., "rHUIL-10 in Subjects with Active Rheumatoid Arthritis (RA): A Phase I and Cytokine Response Study," Arthritis Rheum., 40: S224 (1997).
Merck Manual, "Crohn Disease", https://www.merckmanuals.com/professional/SearchResults?query=Crohn+Disease, downloaded from the Internet Jun. 18, 2015.
Merck Manual, "Overview of Inflammatory Bowel Disease", https://www.merckmanuals.com/professional/gastrointestinal-disorders/inflammatory-bowel-disease-ibd/overview-of-inflammatory-bowel-disease, downloaded from the Internet Jun. 18, 2015.
Merck Manual, "Ulcerative Colitis", https://www.merckmanuals.com/professional/SearchResults?query=Ulcerative+colitis, downloaded from the Internet Jun. 18, 2015.
Mirandola, S. R., et al., "Interferon-beta modifies the peripheral blood cell cytokine secretion in patients with multiple sclerosis," International Immunopharmacology, 9: 824-830 (2009).
Nakase, H., et al., "New Cytokine Delivery System Using Gelatin Microspheres Containing Interleukin-10 for Experimental Inflammatory Bowel Disease," JPET, 301(1): 59-65 (2002).
Needleman, S. B., and Wunsch, C. D., "A General Method Applicable to the Search for Similarities in the Amino Acid Sequence of Two Proteins," J. Mol. Biol., 48: 443-453 (1970).
Ner, S. S., et al., "A Simple and Efficient Procedure for Generating Random Point Mutations and for Codon Replacements Using Mixed Oligodeoxynucleotides," DNA, 7(2): 127-134 (1988).
Niyonsaba, F., et al., "Antimicrobial Peptides Human β-defensins Stimulate Epidermal Keratinocyte Migration, Proliferation and Production of Proinflammatory Cytokines and Chemokines," Journal of Investigative Dermatology, 127: 594-604 (2007).
Office Communication, U.S. Appl. No. 14/131,365, entitled "Oral Treatment of Inflammatory Bowel Disease", filed Jul. 5, 2015, dated Apr. 7, 2015.
Ong, P. Y., et al., "Endogenous Antimicrobial Peptides and Skin Infections in Atopic Dermatitis," N. Engl. J. Med., 347(15): 1151-1160 (2002).
Otte, J-M, et al., "Human Beta Defensin 2 Promotes Intestinal Wound Healing," Gastroenterology, 132(4)(Suppl. 2): A-404 (2007).
Otte, J-M, et al., "Human Beta Defensin 2 Promotes Intestinal Wound Healing In Vitro," J. Cell. Biochem., 104: 2286-2297 (2008).
Overview of Inflammatory Bowel Disease from Merch Manual, pp. 1-5. Accessed Apr. 1, 2015.
Özenci, V, et al., "Multiple sclerosis is associated with an imbalance between tumour necrosis factor-alpha (TNF-α)- and IL-10-secreting blood cells that is corrected by interferon-beta (IFN-β) treatment," Clin. Exp. Immunol., 120: 147-153 (2000).

Pazgier, M., et al., "Human β-defensins," Cell. Mol. Life Sci., 63: 1294-1313 (2006).
Reidhaar-Olson, J. F., and Sauer, R. T., "Combinatorial Cassette Mutagenesis as a Probe of the Informational Content of Protein Sequences," Science, 241(4861): 53-57 (1988).
Rice, P., et al., "EMBOSS: The European Molecular Biology Open Software Suite," TIG, 16(6): 276-277 (2000).
Rowland, T. L., et al., "Differential regulation by thalidomide and dexamethasone of cytokine expression in human peripheral blood mononuclear cells," Immunopharmacology, 40: 11-20 (1998).
Rubbert-Roth, A., and Finckh, A., "Treatment options in patients with rheumatoid arthritis failing initial TNF inhibitor therapy: a critical review," Arthritis Research & Therapy, 11(Suppl. 1) (2009).
Schneider, J. J., et al., "Human defensins," J. Mol. Med., 83: 587-595 (2005).
Schreiber, S., et al., "Safety and Efficacy of Recombinant Human Interleukin 10 in Chronic Active Crohn's Disease," Gastroenterology, 119: 1461-1472 (2000).
Schutte, B. C., et al., "Discovery of five conserved β-defensin gene clusters using a computational search strategy," PNAS, 99(4): 2129-2133 (2002).
Shu, Q., et al., "Protection against Pseudomonas aeruginosa Pneumonia and Sepsis-Induced Lung Injury by Overexpression β-defensin-2 in Rats," SHOCK, 26(4): 365-371 (2006).
Singh, P. K., et al., "Production of β-defensins by human airway epithelia," Proc. Natl. Acad. Sci. USA, 95: 14961-14966 (1998).
Smeets, T. J. M., et al., "Analysis of Serial Synovial Biopsies in Patients with Rheumatoid Arthritis: Description of a Control Group without Clinical Improvement after Treatment with Interleukin 10 or Placebo," J. Rheumatol., 26: 2089-2093 (1999).
Steidler, L., et al., "Treatment of Murine Colitis by Lactococcus lactis Secreting Interleukin-10," Science, 289: 1352-1355 (2000).
Swidsinski, A., et al., "Mucosal Flora in Inflammatory Bowel Disease," Gastroenterology, 122: 44-54 (2002).
Tewary, P., et al., "Human Beta Defensin 3 (HBD3) induces migration and activation of antigen presenting cells and acts as an immune enhancer," The FASEB Journal, 22: 673.10 (2008).
Ulcerative Colitis from Merck Manual, pp. 1-5. Accessed Apr. 1, 2015.
van Roon, J. A. G., et al., "Interleukin 10 Treatment of Patients with Rheumatoid Arthritis Enhances Fcγ Receptor Expression on Monocytes and Responsiveness to Immune Complex Stimulation," J. Rheumatol., 30(4): 648-651 (2003).
Vordenbaumen, S., et al., "Elevated levels of human beta-defensin 2 and human neutrophil peptides in systemic lupus erythematosus," Lupus, 19: 1648-1653 (2010).
Walmsley, M., et al., "Interleukin-10 Inhibition of the Progression of Established Collagen-Induced Arthritis," Arthritis & Rheumatism, 39(3): 495-503 (1996).
Wang, G., et al., "Host-microbe interaction: mechanisms of defensin deficiency in Crohn's disease," Expert Rev. Anti Infect. Ther., 5(6): 1049-1057 (2007).
Wehkamp, J., et al., "Defensin deficiency, intestinal microbes, and the clinical phenotypes of Crohn's disease," J. Leukoc. Biol., 77: 460-465 (2005).
Wehkamp, J., et al., "Human β-defensin 2 but not β-defensin 1 is expressed preferentially in colonic mucosa of inflammatory bowel disease," Eur. J. Gastroenterol. Hepatol., 14: 745-752 (2002).
Wehkamp, J., et al., "Inducible and Constitutive β-Defensins Are Differentially Expressed in Crohn's Disease and Ulcerative Colitis," Inflammatory Bowel Diseases, 9(4): 215-223 (2003).
Wehkamp, J., et al., "Reduced Paneth cell α-defensins in ileal Crohn's disease," PNAS, 102(50): 18129-18134 (2005).
Wirtz, S., and Neurath, M. F., "Mouse models of inflammatory bowel disease," Advanced Drug Delivery Reviews, 59: 1073-1083 (2007).
Written Opinion of the International Searching Authority, International Application No. PCT/EP2012/063137 titled: "Oral Treatment of Inflammatory Bowel Disease", dated Jan. 8, 2014.
Yudoh, K., et al., "Reduced Expression of the Regulatory CD4+ T Cell Subset Is Related to Th1/Th2 Balance and Disease Severity in Rheumatoid Arthritis," Arthritis & Rheumatism, 43(3): 617-627 (2000).
Zhang, X., et al., "IL-10 is involved in the suppression of experimental autoimmune encephalomyelitis by CD25+CD4+ regulatory T cells," International Immunology, 16(2): 249-256 (2004).

Figure 4

Clustal W (2.1) multiple sequence alignments of beta defensin 2

```
SEQ ID NO: 2   UNIPROT_O15263_Human            ----GIGDPVTCLKSGAICHPVFCPRRYKQ
SEQ ID NO: 7   UNIPROT_Q9BDS9_Rhesus_macaque   ----GIGDPVTCLKNGAICHPVFCPRRYKQ
SEQ ID NO: 8   7UNIPROT_Q9TT12_Chimpanzee      ----GISDPVTCLKSGAICHPVFCPRRYKQ
SEQ ID NO: 9   UNIPROT_A4H1Z7_Orangutan        VFGDISNPVTCLRSGAICHPGFCPRRYKH
                                                    *:.******::.*******:

SEQ ID NO: 2   UNIPROT_O15263_Human            IGTCGLPGTKCCKKP
SEQ ID NO: 7   UNIPROT_Q9BDS9_Rhesus_macaque   IGTCGLPGTKCCKKP
SEQ ID NO: 8   UNIPROT_Q9TT12_Chimpanzee       IGTCGLPGTKCCKKP
SEQ ID NO: 9   UNIPROT_A4H1Z7_Orangutan        IGTCGLSVIKCCKKP
                                               *******.
```

Figure 5

Clustal W (2.1) multiple sequence alignments of human beta defensins

```
SEQ ID NO: 1   HBD1    ------DHYNCVSSGGQCLYSACPIFTKIQGTCYRGKAKCCK-------------
SEQ ID NO: 2   HBD2    ----GIGDPVTCLKSGAICHPVFCPRRYKQIGTCGLPGTKCCKKP----------
SEQ ID NO: 5   HBD4S   ----ELDRICGYGTARCR-KKCRSQEYRIGRCPN-TYACCLRK------------
SEQ ID NO: 4   HBD4L   ---EFELDRICGYGTARCR-KKCRSQEYRIGRCPN-TYACCLRKWDESLLNRTKP
SEQ ID NO: 3   HBD3    GINTLQKYYCRVRGGRCAVLSCLPKEEQIGKCSTRGRKCCRRKK-----------
                              *    .   *            * *            **
```

ORAL TREATMENT OF INFLAMMATORY BOWEL DISEASE

RELATED APPLICATIONS

This application is a continuation of U.S. application Ser. No. 14/131,364 which is the U.S. National Stage of International Application No. PCT/EP2012/063137, filed Jul. 5, 2012, which designates the U.S., published in English, and claims priority under 35 U.S.C. §§119 or 365(c) to European Application No. 11173351.5, filed Jul. 8, 2011 and U.S. Provisional Application No. 61/506,437, filed on Jul. 11, 2011. The entire teachings of the above applications are incorporated herein by reference.

INCORPORATION BY REFERENCE OF MATERIAL IN ASCII TEXT FILE

This application incorporates by reference the Sequence Listing contained in the following ASCII text file:
a) File name: 47681005001_SUB_SEQLIST.txt; created Mar. 31, 2017, 5 KB in size.

FIELD OF INVENTION

The present invention relates to treatment of an inflammatory bowel disease by simultaneous or successive parental and oral administration of a mammalian beta defensin.

BACKGROUND OF INVENTION

Human Defensins

Among many other elements, key components of innate immunity are the antimicrobial peptides (AMPs) that individually show considerable selectivity, but collectively are able to rapidly kill a broad spectrum of bacteria, viruses and fungi. The biological significance of AMPs is emphasized by their ubiquitous distribution in nature and they are probably produced by all multicellular organisms. In humans the predominant AMPs are the defensins. The human defensins are small cationic peptides that can be divided into α- and β-defensins based on the topology of their three intramolecular cysteine disulphide bonds. The α-defensins can be further subdivided into those that were first isolated from neutrophil granules (HNP1-4) and those that are expressed by Paneth cells in the crypts of the small intestine (HD5 and HD6). The β-defensins are mainly produced by epithelial cells in various tissues and organs including the skin, trachea, gastrointestinal tract, urogenital system, kidneys, pancreas and mammary gland. The best characterized members of the β-defensin family are hBD1-3. However, using various bioinformatics tools almost 40 open reading frames encoding putative β-defensin homologues have been annotated in the human genome. Some of the human defensins are produced constitutively, whereas others are induced by proinflammatory cytokines or exogenous microbial products.

It has become increasingly clear that the human defensins in addition to their direct antimicrobial activity also have a wide range of immunomodulatory/alternative properties. These include the induction of various chemokines and cytokines, chemotactic and apoptotic activities, induction of prostaglandin, histamine and leukotriene release, inhibition of complement, stimulation of dendritic cell maturation through toll-like receptor signalling and stimulation of pathogen clearance by neutrophils. Furthermore, the human defensins also play a role in wound healing, proliferation of epithelial and fibroblast cells, angiogenesis and vasculogenesis.

There is increasing evidence that the human defensins play an important role in many infectious and inflammatory diseases. Overexpression of human defensins is often observed in inflamed and/or infected skin most likely because of local induction by microbial components or endogenous proinflammatory cytokines. In psoriasis hBD2 and hBD3 are overabundant and in lesional epithelium of patients with acne vulgaris or superficial folliculitis a significant upregulation of hBD2 has been observed. On the other hand, downregulation of hBD2 and hBD3 has been associated with atopic dermatitis. Ileal Crohn's disease has been associated with deficient expression of HD5 and HD6 and in Crohn's disease in the colon expression of hBD2-4 are downregulated.

Inflammatory Bowel Diseases

Inflammatory bowel diseases (IBD) are defined by chronic, relapsing intestinal inflammation of obscure origin. IBD refers to two distinct disorders, Crohn's disease and ulcerative colitis (UC). Both diseases appear to result from the unrestrained activation of an inflammatory response in the intestine. This inflammatory cascade is thought to be perpetuated through the actions of proinflammatory cytokines and selective activation of lymphocyte subsets. In patients with IBD, ulcers and inflammation of the inner lining of the intestines lead to symptoms of abdominal pain, diarrhea, and rectal bleeding. Ulcerative colitis occurs in the large intestine, while in Crohn's, the disease can involve the entire GI tract as well as the small and large intestines. For most patients, IBD is a chronic condition with symptoms lasting for months to years. It is most common in young adults, but can occur at any age. It is found worldwide, but is most common in industrialized countries such as the United States, England, and northern Europe. It is especially common in people of Jewish descent and has racial differences in incidence as well. Recent studies have identified variations in specific genes, including ATG16L1, IL23R, IRGM, and NOD2, that influence the risk of developing Crohn disease. As many as 30 human genes have been identified which contribute to ulcerative colitis susceptibility.

The clinical symptoms of IBD are intermittent rectal bleeding, cramping abdominal pain, weight loss and diarrhea. Diagnosis of IBD is based on the clinical symptoms, the use of a barium enema, but direct visualization (sigmoidoscopy or colonoscopy) is the most accurate test. Protracted IBD is a risk factor for colon cancer, and treatment of IBD can involve medications and surgery.

Some patients with UC only have disease in the rectum (proctitis). Others with UC have disease limited to the rectum and the adjacent left colon (proctosigmoiditis). Yet others have UC of the entire colon (universal IBD). Symptoms of UC are generally more severe with more extensive disease (larger portion of the colon involved with disease).

The prognosis for patients with disease limited to the rectum (proctitis) or UC limited to the end of the left colon (proctosigmoiditis) is better than that of full colon UC. Brief periodic treatments using oral medications or enemas may be sufficient. In those with more extensive disease, blood loss from the inflamed intestines can lead to anemia, and may require treatment with iron supplements or even blood transfusions. Rarely, the colon can acutely dilate to a large size when the inflammation becomes very severe. This condition is called toxic megacolon. Patients with toxic megacolon are extremely ill with fever, abdominal pain and distention, dehydration, and malnutrition. Unless the patient improves rapidly with medication, surgery is usually necessary to prevent colon rupture.

Crohn's disease can occur in all regions of the gastrointestinal tract. With this disease intestinal obstruction due to inflammation and fibrosis occurs in a large number of patients. Granulomas and fistula formation are frequent complications of Crohn's disease. Disease progression consequences include intravenous feeding, surgery and colostomy.

IBD may be treated medicinally. The most commonly used medications to treat IBD are anti-inflammatory drugs such as the salicylates. The salicylate preparations have been effective in treating mild to moderate disease. They can also decrease the frequency of disease flares when the medications are taken on a prolonged basis. Examples of salicylates include sulfasalazine, azulfidine, olsalazine, and mesalamine. All of these medications are given orally in high doses for maximal therapeutic benefit. These medicines are not without side effects. Azulfidine can cause upset stomach when taken in high doses, and rare cases of mild kidney inflammation have been reported with some salicylate preparations.

Corticosteroids are more potent and faster-acting than salicylates in the treatment of IBD, but potentially serious side effects limit the use of corticosteroids to patients with more severe disease. Side effects of corticosteroids usually occur with long term use. They include thinning of the bone and skin, increased susceptibility to infections, diabetes, hypertension, glaucoma, muscle wasting/weakness, rounding of the face, psychiatric disturbances, and, on rare occasions, destruction of hip joints.

In IBD patients that do not respond to salicylates or corticosteroids, medications that suppress the immune system are used. Examples of immunosuppressants include azathioprine and 6-mercaptopurine. Immunosuppressants used in this situation help to control IBD and allow gradual reduction or elimination of corticosteroids. However, immunosuppressants render the patient immuno-compromised and susceptible to many other diseases.

A well recognized model for studying IBD is the DSS colitis mouse model, as described in Kawada et al. "Insights from advances in research of chemically induced experimental models of human inflammatory bowel disease", World J. Gastroenterol., Vol. 13 (42), pp. 5581-5593 (2007); and Wirtz and Neurath "Mouse models of inflammatory bowel disease", Advanced Drug Delivery Reviews, Vol. 59 (11), 1073-1083 (2007).

Treatment of inflammatory bowel disease (IBD) has traditionally been accomplished with administration of aminosalicylates, corticosteroids, thiopurines, methotrexate, and anti-tumor necrosis factor agents. Human beta defensins has long be thought to play a role in the occurrence and/or treatment of IBD.

Clearly there is a great need for agents capable of preventing and treating IBD.

WO 2007/081486 discloses the use of several human defensins in the treatment of inflammatory bowel disease. The inventors suggested that defensins administered orally to Crohn's patients, in a formulation that allow their release at proper locations in the intestinal lumen, would reduce the number of invading bacteria, re-establish a normal epithelial barrier function and, thus, reduce the severity of the inflammatory disease.

According to WO 2007/081486, the function of the defensins is to directly target and kill bacteria in the lumen to prevent them from invading the epithelial tissue. That is, the function of the defensins is purely as an anti-infective compound.

SUMMARY OF INVENTION

The present invention demonstrates an anti-inflammatory activity of orally administered hBD2 in the model of DSS colitis induced in the mouse after a 10-day treatment period.

These data indicates the beneficial treatment effect of IBD associated with simultaneous or successive oral and parenteral administration of a mammalian beta defensin.

In one aspect the present invention relates to a process for administering a mammalian beta defensin to an individual suffering from an inflammatory bowel disease, the process comprising simultaneous or successive oral and parenteral administration of said mammalian beta defensin.

In one aspect the present invention relates to oral administration of mammalian beta defensins for prophylactic treatment or as a method of keeping a subject suffering from IBD in remission.

In one aspect the invention relates to prolonging this period of remission after oral administration of a mammalian beta defensin.

In patients suffering from IBD an acute resurgence of the original symptoms may appear every so often; this is known as a "relapse". Depending on the circumstances, it may go away on its own or require medication. The time between relapse may be anywhere from weeks to years, and varies between patients. In one aspect of the present invention oral administration of a mammalian beta defensin reduces the occurrence of relapse in a subject suffering from an IBD.

As described in the definition section of this application IBD is a group of inflammatory conditions of the colon and small intestine. The major types of IBD are Crohn's disease and ulcerative colitis (UC). In one preferred embodiment of the present invention the IBD to be treated is mild active and/or moderately to severely active Crohn's disease and ulcerative colitis.

In one aspect of the present invention oral administration of mammalian beta defensins may be used for reducing neutrophil invasion in the epithelial lining of the colon. This reduction may be located to either the proximal or the distal colon.

In another aspect of the present invention oral administration of mammalian beta defensin may be used for treatment of inflammation in the colon.

In yet another aspect of the present invention oral administration of a mammalian beta defensin may be used for modulating cytokine production at the epithelial lining in the gastrointestinal tract. The modulation is preferably a downregulation of the activity of at least one cytokine selected from the group consisting of the pro-inflammatory cytokines and chemokines Preferably the modulation is a downregulation of the activity of at least one cytokine selected from the group consisting of the pro-inflammatory IL-23, IL-1$\beta$ and TNF$\alpha$, and/or an upregulation of the activity of the anti-inflammatory cytokine IL-10.

group values at a given date are shown as *P<0.05; P<0.01 *P<0.001 (Kruskal-Wallis Test for non-parametric data).

Figure 2:
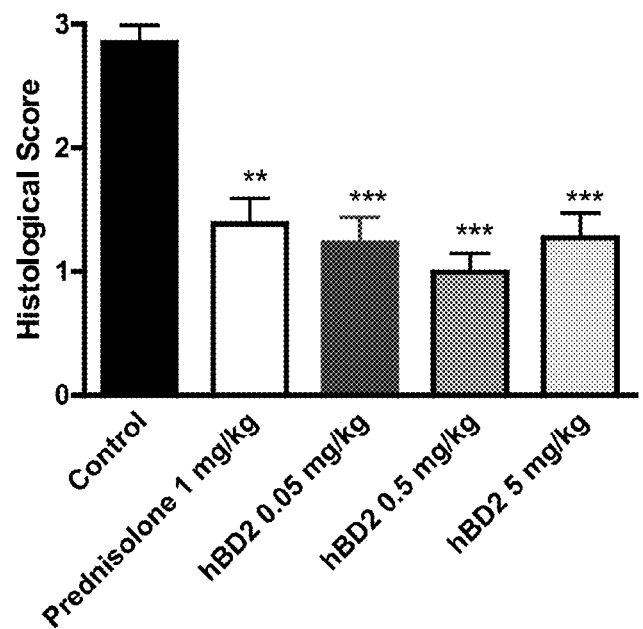

FIG. 2. Histological score of proximal colon samples. Results are shown as the mean±the standard error of the mean for n=10 animals per group. Significant differences from control (vehicle) group values are shown as P<0.01; *P<0.001 (Kruskal-Wallis Test+post–test of Dunn for non-parametric data).

Figure 3:
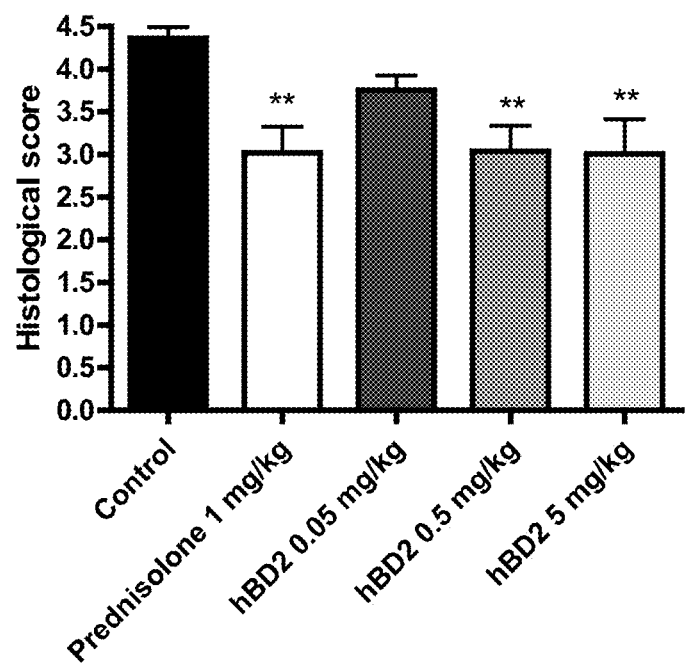

FIG. 3. Histological score of distal colon samples. Results are shown as the mean±the standard error of the mean for n=10 animals per group. Significant differences from control (vehicle) group values are shown as **P<0.01 (Kruskal-Wallis Test+post–test of Dunn for non-parametric data).

FIG. 4. Clustal W (2.1) multiple sequence alignment of human, Rhesus macaque, chimpanzee and orangutan beta defensin 2.

* indicates positions which have a single, fully conserved residue.
: indicates that one of the following 'strong' groups is fully conserved: S, T, and A; N, E, Q, and K; N, H, Q, and K; N, D, E, and Q; Q, H, R, and K; M, I, L, and V; M, I, L, and F; H and Y; F, Y, and W.
. indicates that one of the following 'weaker' groups is fully conserved: C, S, and A; A, T, and V; S, A, and G; S, T, N, and K; S, T, P, and A; S, G, N, and D; S, N, D, E, Q, and K; N, D, E, Q, H, and K; N, E, Q, H, R, and K; V, L, I, and M; H, F, and Y.

FIG. 5. Clustal W (2.1) multiple sequence alignment of human defensin 1-4.

* indicates positions which have a single, fully conserved residue.
: indicates that one of the following 'strong' groups is fully conserved: S, T, and A; N, E, Q, and K; N, H, Q, and K; N, D, E, and Q; Q, H, R, and K; M, I, L, and V; M, I, L, and F; H and Y; F, Y, and W.
. indicates that one of the following 'weaker' groups is fully conserved: C, S, and A; A, T, and V; S, A, and G; S, T, N, and K; S, T, P, and A; S, G, N, and D; S, N, D, E, Q, and K; N, D, E, Q, H, and K; N, E, Q, H, R, and K; V, L, I, and M; H, F, and Y.

DETAILED DESCRIPTION OF THE INVENTION

Definitions

Defensin: The term "defensin" as used herein refers to polypeptides recognized by a person skilled in the art as belonging to the defensin class of antimicrobial peptides. To determine if a polypeptide is a defensin according to the invention, the amino acid sequence may be compared with the hidden markov model profiles (HMM profiles) of the PFAM database by using the freely available HMMER software package.

The PFAM defensin families include for example Defensin_1 or "Mammalian defensin" (accession no. PF00323), and Defensin_2 or Defensin_beta or "Beta Defensin" (accession no. PF00711).

The defensins of the invention belong to the beta defensin class. The defensins from the beta defensin class share common structural features known to the person skilled in the art, such as the cysteine pattern.

Examples of defensins, according to the invention, include human beta defensin 1 (hBD1; see SEQ ID NO:1), human beta defensin 2 (hBD2; see SEQ ID NO:2), human beta defensin 3 (hBD3; see SEQ ID NO:3), human beta defensin 4 (hBD4; see SEQ ID NO:4), and mouse beta defensin 3 (mBD3; see SEQ ID NO:6).

Identity: The relatedness between two amino acid sequences or between two nucleotide sequences is described by the parameter "identity".

For purposes of the present invention, the degree of identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends in Genetics* 16: 276-277; <<http://emboss.org>>), preferably version 3.0.0 or later. The optional parameters used are gap open penalty of 10, gap extension penalty of 0.5, and the EBLOSUM62 (EMBOSS version of BLOSUM62) substitution matrix.

The output of Needle labeled "longest identity" (obtained using the -nobrief option) is used as the percent identity and is calculated as follows:

(Identical Residues×100)/(Length of Alignment–Total Number of Gaps in Alignment.

Isolated polypeptide: The term "isolated variant" or "isolated polypeptide" as used herein refers to a variant or a polypeptide that is isolated from a source. In one aspect, the variant or polypeptide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by RP-HPLC analysis.

Substantially pure polypeptide: The term "substantially pure polypeptide" denotes herein a polypeptide preparation that contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polypeptide material with which it is natively or recombinantly associated. It is, therefore, preferred that the substantially pure polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation. The polypeptides of the present invention are preferably in a substantially pure form. This can be accomplished, for example, by preparing the polypeptide by well-known recombinant methods or by classical purification methods or by chemical synthesis.

Remission: The term "Remission" denotes herein periods with disease control versus active disease which are often referred to as "attack".

Relapse: The term "relapse" denotes herein re-occurrence of the symptoms of IBD. The most common early symptoms of IBD are chronic diarrhea (which is sometimes bloody), cramping abdominal pain, fever, loss of appetite, and weight loss. Symptoms may continue for days or weeks and may resolve without treatment. IBD relapses at irregular intervals throughout the lifespan of a subject. Relapse can be mild or severe, brief or prolonged. Severe relapses can lead to intense pain, dehydration, and blood loss.

Inflammatory bowel disease (IBD): inflammatory bowel disease (IBD) is a group of inflammatory conditions of the colon and small intestine. The major types of IBD are Crohn's disease and ulcerative colitis (UC).

Accounting for far fewer cases are other forms of IBD, which are not always classified as typical IBD:
Collagenous colitis
Lymphocytic colitis
Ischaemic colitis
Diversion colitis
Behçet's disease
Indeterminate colitis The main difference between Crohn's disease and UC is the location and nature of the inflammatory changes. Crohn's can affect any part of the gastrointestinal tract, from mouth to anus (skip lesions), although a majority of the cases start in the terminal ileum. Ulcerative colitis, in contrast, is restricted to the colon and the rectum.

Treatment: The terms "treatment" and "treating" as used herein refer to the management and care of a patient for the purpose of combating a condition, disease or disorder. The term is intended to include the full spectrum of treatments for a given condition from which the patient is suffering, such as administration of the active compound for the purpose of: alleviating or relieving symptoms or complications; delaying the progression of the condition, disease or disorder; curing or eliminating the condition, disease or disorder; and/or preventing the condition, disease or disorder, wherein "preventing" or "prevention" is to be understood to refer to the management and care of a patient for the purpose of hindering, reducing or delaying the development of the condition, disease or disorder, and includes the administration of the active compounds to prevent or reduce the risk of the onset of symptoms or complications. The patient to be treated is preferably a mammal, in particular a human being. The patients to be treated according to the present invention can be of various ages.

Mammal Beta Defensins

The present invention relates to pharmaceutical uses of mammal beta defensins, such as mouse, monkey or human beta defensins, more preferably Hominidae beta defensins, more preferably human beta defensin. in the treatment of inflammatory bowel diseases, such as ulcerative colitis and/or Crohns disease.

In an embodiment, the mammal beta defensins of the invention have a degree of identity of at least 80%, preferably at least 85%, more preferably at least 90%, and most preferably at least 95% to any of the amino acid sequences of SEQ ID NO:1, SEQ ID NO:2, SEQ ID NO:3, SEQ ID NO:4, SEQ ID NO:5 and/or SEQ ID NO:6. In a preferred embodiment, the mammal beta defensins of the invention have a degree of identity of at least 80%, preferably at least 85%, more preferably at least 90%, and most preferably at least 95% to any of the amino acid sequences of SEQ ID NO:1, SEQ ID NO:2, SEQ ID NO:3 and/or SEQ ID NO:4. In a more preferred embodiment, the mammal beta defensins of the invention consist of human beta defensin 1 (SEQ ID NO:1), human beta defensin 2 (SEQ ID NO:2), human beta defensin 3 (SEQ ID NO:3), human beta defensin 4 (SEQ ID NO:4), a variant of human beta defensin 4 (SEQ ID NO:5) and/or mouse beta defensin 3 (SEQ ID NO:6). In an even more preferred embodiment, the mammal beta defensins of the invention consist of human beta defensin 1 (SEQ ID NO:1), human beta defensin 2 (SEQ ID NO:2), human beta defensin 3 (SEQ ID NO:3) and/or human beta defensin 4 (SEQ ID NO:4).

In a preferred embodiment, the mammal beta defensins of the invention have a degree of identity of at least 80%, preferably at least 85%, more preferably at least 90%, and most preferably at least 95% to the amino acid sequence of SEQ ID NO:2. In a preferred embodiment, the mammal beta defensins of the invention consist of human beta defensin 2 (SEQ ID NO:2).

In yet another embodiment, the mammal beta defensins of the invention consist of human beta defensins and/or mouse beta defensins, and functionally equivalent variants thereof. Preferably, the mammal beta defensins consist of human beta defensin 1, human beta defensin 2, human beta defensin 3, human beta defensin 4, Chimpanzee beta defensin 2, Macaque beta defensin 2, and mouse beta defensin 3, and functionally equivalent variants thereof. More preferably, the mammal beta defensins of the invention consist of human beta defensin 2, and functionally equivalent variants thereof.

The mammal beta defensins of the invention are also referred to as compounds of the preferred embodiments.

In the context of the present invention, a "functionally equivalent variant" of a mammal (e.g. human) beta defensin is a modified mammal (e.g. human) beta defensin exhibiting approx. the same effect on an inflammatory bowel disease as the parent mammal (e.g. human) beta defensin. Preferably, it also exhibits approx. the same effect on the activity of pro-inflammatory cytokines and chemokines and/or anti-inflammatory cytokine as the mammal (e.g. human) beta defensin. In one embodiment the effect on the activity of pro-inflammatory and anti-inflammatory cytokines is measured as described in WO 2010/007166 in Example 4 and 6. The effect may be measured in a human cell selected from the group consisting of human PBMCs, human CD14+ monocyte-derived dendritic cells, a human monocyte cell line, and human immature dendritic cells, preferably human PBMC.

According to the invention, a functionally equivalent variant of a mammal (e.g. human) beta defensin may comprise 1-5 amino acid modifications, preferably 1-4 amino acid modifications, more preferably 1-3 amino acid modifications, most preferably 1-2 amino acid modification(s), and in particular one amino acid modification, as compared to the mammal (e.g. human) beta defensin amino acid sequence. Preferably compared to human beta defensin 2, having SEQ ID NO 2.

The term "modification" means herein any chemical modification of a mammal (e.g. human) beta defensin. The modification(s) can be substitution(s), deletion(s) and/or insertions(s) of the amino acid(s) as well as replacement(s) of amino acid side chain(s); or use of unnatural amino acids with similar characteristics in the amino acid sequence. In particular the modification(s) can be amidations, such as amidation of the C-terminus.

Preferably, amino acid modifications are of a minor nature, that is conservative amino acid substitutions or insertions that do not significantly affect the folding and/or activity of the polypeptide; single deletions; small amino- or carboxyl- terminal extensions; or a small extension that facilitates purification by changing net charge or another function, such as a poly-histidine tag, an antigenic epitope or a binding domain. In one embodiment the small extension, such as a poly-histidine tag, an antigenic epitope or a binding domain is attached to the mammalian (e.g. human) beta defensin through a small linker peptide of up to about 20-25 residues and said linker may contain a restriction enzyme cleavage site. The Clustal W alignment in FIG. 4 or FIG. 5 can be used to predict which amino acid residues can be substituted without substantially affecting the biological activity of the protein. The sequences were aligned using Clustal W 2.1 (<<http://www.genomelp/tools/clustalw/>>)

and the following settings: Gap Open Penalty: 10, Gap Extension Penalty: 0.05, Weight Transition: NO, Hydrophilic Residues for Proteins: GPSNDQE, Hydrophilic Gaps: YES, Weight Matrix: BLOSUM (for PROTEIN).

Substitutions within the following group (Clustal W, 'strong' conservation group) are to be regarded as conservative substitutions within the meaning of the present invention S, T, and A; N, E, Q, and K; N, H, Q, and K; N, D, E, and Q; Q, H, R, and K; M, I, L, and V; M, I, L, and F; H and Y; F, Y, and W.

Substitutions within the following group (Clustal W, 'weak' conservation group) are to be regarded as semiconservative substitutions within the meaning of the present invention C, S, and A; A, T, and V; S, A, and G; S, T, N, and K; S, T, P, and A; S, G, N, and D; S, N, D, E, Q, and K; N, D, E, Q, H, and K; N, E, Q, H, R, and K; V, L, I, and M; H, F, and Y.

Examples of conservative substitutions are substitutions made within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter specific activity are known in the art and are described, for example, by H. Neurath and R. L. Hill, 1979, In, *The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Essential amino acids in a mammal beta defensin can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for biological activity (i.e., activity against an inflammatory bowel disease and/or suppression of TNF-alpha activity) to identify amino acid residues that are critical to the activity of the molecule. See also, Hilton et al., 1996, *J. Biol. Chem.* 271: 4699-4708. The identities of essential amino acids can also be inferred from analysis of identities with polypeptides which are related to mammal beta defensins (see Clustal W alignment in FIG. 4 and FIG. 5).

Single or multiple amino acid substitutions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochem.* 30:10832-10837; U.S. Pat. No. 5,223,409; WO 92/06204), and region-directed mutagenesis (Derbyshire et al., 1986, *Gene* 46:145; Ner et al., 1988, *DNA* 7:127).

An N-terminal extension of the polypeptides of the invention may suitably consist of from 1 to 50 amino acids, preferably 2-20 amino acids, especially 3-15 amino acids. In one embodiment N-terminal peptide extension does not contain an Arg (R). In another embodiment the N-terminal extension comprises a kex2 or kex2-like cleavage site as will be defined further below. In a preferred embodiment the N-terminal extension is a peptide, comprising at least two Glu (E) and/or Asp (D) amino acid residues, such as an N-terminal extension comprising one of the following sequences: EAE, EE, DE and DD.

When the result of a given substitution cannot be predicted with certainty, the derivatives may be readily assayed according to the methods described herein above to determine the presence or absence of biological activity.

Methods and Uses

Human beta defensin 2 was found to significantly reduce the severity of disease parameters in a 10-Day Dextran Sodium Sulphate (DSS)-induced colitis model in the mouse; thus showing potent activity as a medicament for treatment of inflammatory bowel diseases, such as ulcerative colitis and Crohn's disease.

The present invention therefore provides methods of prophylactic treatment for an inflammatory bowel diseases or as a method of keeping a subject suffering from IBD in remission, which treatment comprises administering orally to a subject in need of such treatment an effective amount of a mammal beta defensin, such as human beta defensin 2, e.g., in the form of a pharmaceutical composition.

In one embodiment the invention relates to prolonging this period of remission after oral administration of a mammalian beta defensin or reducing the occurrence of relapse in a subject suffering from IBD.

Inflammatory bowel disease according to this invention relates to Crohn's Disease and ulcerative colitis. In a preferred embodiment the stage of Crohn's Disease to be treated using oral administration of a mammalian beta defensin is remission and/or mild active Crohn's Disease. In another preferred embodiment the stage of ulcerative colitis to be treated using oral administration of a mammalian beta defensin is remission stage of ulcerative colitis (e.g. pancolitis/remission, left-sided colitis/remission and therapy-refractory disease in remission).

In one embodiment of the present invention oral administration of mammalian beta defensions may be used for reducing neutrophil invasion in the epithelial lining of the colon. This reduction may be located to either the proximal or the distal colon.

In another embodiment of the present invention oral administration of mammalian beta defensin may be used for treatment of inflammation in the colon.

In yet another embodiment of the present invention oral administration of a mammalian beta defensin may be used for modulating cytokine production at the epithelial lining in the gastrointestinal tract.

The modulation is preferably a downregulation of the activity of at least one cytokine selected from the group consisting of the pro-inflammatory cytokines and chemokines Preferably the modulation is a downregulation of the activity of at least one cytokine selected from the group consisting of the pro-inflammatory IL-23, IL-1β and TNFα, and/or an upregulation of the activity of the anti-inflammatory cytokine IL-10.

In another embodiment the present invention provides methods of treating inflammatory bowel diseases, which treatment comprises administering simultaneous or successive parenteral and oral administration of an effective amount of a mammalian beta defensin in the form of a pharmaceutical composition. During an active breakout ("attack") of inflammatory bowel disease the subject suffering from said IBD may in one embodiment be subjected to parenteral administration of a mammalian beta defensin, such as human beta defensin 2, combined with or followed by oral administration of said mammalian beta defensin during the periods of remission.

In an embodiment, the method of treatment with hBD2 results in a significant inhibition of the disease activity index (DAI) in an in vivo model of IBD when administered twice daily, at 3 dose levels by the oral route and hBD2 also demonstrated a very significant anti-inflammatory activity in the same model.

Mammal beta defensins can be employed therapeutically in compositions formulated for administration by any conventional route. In one embodiment of the present invention mammalian beta defensins are administered orally.

In another embodiment of the present invention mammalian beta defensins are administered by simultaneous or successive oral and parenteral administration.

Oral administration is normally for enteral drug delivery, wherein the agent is delivered through the enteral mucosa.

Parenteral administration is any administration route not being the oral/enteral route whereby the medicament avoids first-pass degradation in the liver. Accordingly, parenteral administration includes any injections and infusions, for example bolus injection or continuous infusion, such as intravenous administration, intramuscular administration, subcutaneous administration.

The subcutaneous and intramuscular forms of parenteral administration are generally preferred.

Within yet other embodiments, compositions, of preferred embodiments may be formulized as a lyophilizate, utilizing appropriate excipients that provide stability as a lyophilizate, and subsequent to rehydration.

Pharmaceutical compositions containing a mammal beta defensin, such as a human beta defensin, can be manufactured according to conventional methods, e.g., by mixing, granulating, coating, dissolving or lyophilizing processes.

Pharmaceutical compositions of preferred embodiments comprise a mammal beta defensin, such as a human beta defensin, and a pharmaceutically acceptable carrier and/or diluent.

Pharmaceutically acceptable carriers and/or diluents are familiar to those skilled in the art. For compositions formulated as liquid solutions, acceptable carriers and/or diluents include saline and sterile water, and may optionally include antioxidants, buffers, bacteriostats, and other common additives.

Parenteral administration may be in the form of injections and infusions and said formulations may take such forms as suspensions, solutions, or emulsions in oily or aqueous vehicles. Alternatively, the active ingredient may be in powder form, obtained by aseptic isolation of sterile solid or by lyophilisation from solution for constitution before use with a suitable vehicle, e.g., sterile, pyrogen-free water. The formulations can be presented in unit-dose or multi-dose sealed containers, such as ampoules, vials, pre-filled syringes, infusion bags, or can be stored in a freeze-dried (lyophilized) condition requiring only the addition of the sterile liquid excipient, for example, water, for injections, immediately prior to use.

Examples of oily or non-aqueous carriers, diluents, solvents or vehicles include propylene glycol, polyethylene glycol, vegetable oils, and injectable organic esters, and may contain formulatory agents such as preserving, wetting, emulsifying or suspending, stabilizing and/or dispersing agents.

The compound of the present invention may be formulated in a wide variety of formulations for oral administration. Solid form preparations may include powders, tablets, drops, capsules, cachets, lozenges, and dispersible granules. Other forms suitable for oral administration may include liquid form preparations including emulsions, syrups, elixirs, aqueous solutions, aqueous suspensions, toothpaste, gel dentrifice, chewing gum, or solid form preparations which are intended to be converted shortly before use to liquid form preparations, such as solutions, suspensions, and emulsions.

In powders, the carrier is a finely divided solid which is a mixture with the finely divided active component. In tablets, the active component is mixed with the carrier having the necessary binding capacity in suitable proportions and compacted in the shape and size desired. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like.

Drops according to the present invention may comprise sterile or non-sterile aqueous or oil solutions or suspensions, and may be prepared by dissolving the active ingredient in a suitable aqueous solution, optionally including a bactericidal and/or fungicidal agent and/or any other suitable preservative, and optionally including a surface active agent. Suitable solvents for the preparation of an oily solution include glycerol, diluted alcohol and propylene glycol.

Emulsions may be prepared in solutions in aqueous propylene glycol solutions or may contain emulsifying agents such as lecithin, sorbitan monooleate, or acacia. Aqueous solutions can be prepared by dissolving the active component in water and adding suitable colorants, flavors, stabilizing and thickening agents. Aqueous suspensions can be prepared by dispersing the finely divided active component in water with viscous material, such as natural or synthetic gums, resins, methylcellulose, sodium carboxymethylcellulose, and other well known suspending agents.

The formulation can contain (in addition to a mammal beta defensin, and other optional active ingredients) carriers, fillers, disintegrators, flow conditioners, sugars and sweeteners, fragrances, preservatives, stabilizers, wetting agents, emulsifiers, solubilizers, salts for regulating osmotic pressure, buffers, diluents, dispersing and surface-active agents, binders, lubricants, and/or other pharmaceutical excipients as are known in the art.

One skilled in this art may further formulate mammal beta defensins in an appropriate manner, and in accordance with accepted practices, such as those described in Remington's Pharmaceutical Sciences, Gennaro, Ed., Mack Publishing Co., Easton, Pa. 1990.

A mammal beta defensin, such as a human beta defensin, can be used alone, or in combination therapies with one, two, or more other pharmaceutical compounds or drug substances, and/or with one or more pharmaceutically acceptable excipient(s).

In Vitro Synthesis

Mammal beta defensins may be prepared by in vitro synthesis, using conventional methods as known in the art. Various commercial synthetic apparatuses are available, for example automated synthesizers by Applied Biosystems Inc., Beckman, etc. By using synthesizers, naturally occurring amino acids may be substituted with unnatural amino acids, particularly D-isomers (or D-forms) e.g. D-alanine and D-isoleucine, diastereoisomers, side chains having different lengths or functionalities, and the like. The particular sequence and the manner of preparation will be determined by convenience, economics, purity required, and the like.

Chemical linking may be provided to various peptides or proteins comprising convenient functionalities for bonding, such as amino groups for amide or substituted amine formation, e.g. reductive amination, thiol groups for thioether or disulfide formation, carboxyl groups for amide formation, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

Mammal beta defensins, or functional equivalents thereof, may also be isolated and purified in accordance with conventional methods of recombinant synthesis. Recombinant synthesis may be performed using appropriate expression vectors and a eukaryotic expression system. A solution may be prepared of the expression host and the media and the defensins present purified using HPLC, exclusion chromatography, gel electrophoresis, affinity chromatography, or other purification technique. Methods for recombinant expression of human beta defensin 2 in *E. coli* are disclosed in WO 2010/007166 (Novozymes).

Dosages

A mammal beta defensin, such as a human beta defensin, is preferably employed in pharmaceutical compositions in an amount which is effective to treat an inflammatory bowel disease, preferably with acceptable toxicity to the patient. For such treatment, the appropriate dosage will, of course, vary depending upon, for example, the chemical nature and the pharmacokinetic data of a compound of the present invention used, the individual host, the mode of administration and the nature and severity of the conditions being treated. However, in general, for satisfactory results in larger mammals, for example humans, an indicated daily dosage is preferably from about 0.0001 mg/kg body weight to about 10 mg/kg body weight, more preferably from about 0.001 mg/kg body weight to about 10 mg/kg body weight; such as 0.005 mg/kg body weight to 5 mg/kg body weight, more preferably from about 0.01 mg/kg body weight to about 10 mg/kg body weight, preferably from about 0.1 mg/kg body weight to about 10 mg/kg body weight, for example, administered in divided doses up to one, two, three, or four times a day. The compounds of preferred embodiments can be administered to larger mammals, for example humans, by similar modes of administration at similar dosages than conventionally used.

In one embodiment the daily dosage is preferably from 0.0001-10 mg/kg bodyweight, more preferably 0.001-10 mg/kg body weight, more preferably 0.005-5 mg/kg body weight.

In certain embodiments, the pharmaceutical compositions of preferred embodiments can include a mammal beta defensin, such as a human beta defensin, in an amount of about 0.5 mg or less to about 1500 mg or more per unit dosage form depending upon the route of administration, preferably from about 0.5, 0.6, 0.7, 0.8, or 0.9 mg to about 150, 200, 250, 300, 350, 400, 450, 500, 600, 700, 800, 900, or 1000 mg, and more preferably from about 1, 2, 3, 4, 5, 6, 7, 8, 9, 10, 15, 20, or 25 mg to about 30, 35, 40, 45, 50, 55, 60, 65, 70, 75, 80, 85, 90, 95, or 100 mg. In certain embodiments, however, lower or higher dosages than those mentioned above may be preferred. Appropriate concentrations and dosages can be readily determined by one skilled in the art.

In one embodiment, the mammalian beta defensin is administered at least once daily, such as at least twice daily, for example at least 3 times daily, such as at least 4 times daily.

The present invention is further described by the following examples that should not be construed as limiting the scope of the invention.

EXAMPLES

Example 1

10-Day Dextran Sodium Sulphate (DSS)-Induced Colitis Model in the Mouse

The aim of the following study was to determine the anti-inflammatory activity of human beta defensin 2 in an acute (10-days) model of inflammatory bowel disease (colitis) induced by oral dextran sodium sulphate (DSS) administration in the mouse.

The DSS colitis mouse model is a well recognized model for studying inflammatory bowel disease, as described in Kawada et al. "Insights from advances in research of chemically induced experimental models of human inflammatory bowel disease", World J. Gastroenterol., Vol. 13 (42), pp. 5581-5593 (2007); and Wirtz and Neurath "Mouse models of inflammatory bowel disease", Advanced Drug Delivery Reviews, Vol. 59 (11), 1073-1083 (2007).

Materials

Test Items

Human beta defensin 2 (hBD2); Methylprednisolone 21-hemisuccinate ("prednisolone"), PBS buffer (GIBCO).

Experimental Animals

Male C57BL/6 mice (Harlan Interfauna *Iberica*, Barcelona, Spain) were used in the study, as this is a species and sex that has been demonstrated to develop significant inflammation of the colon when administered a 2% solution of DSS in the drinking water over a period of 10 days.

Identification

Animals were identified by number and letter codes on their tails. Additionally, each cage was identified by a colour-coded card indicating the number and sex of the animals, the test item code or name, dose level, administration route, treatment period, group number, study code and study director's name.

Weight

The average body weight of the animals on the day of start of the study was 22.4±0.16 g.

Acclimatization

Minimum of 7 days prior to the start of the study, under the same conditions as those of the main study.

Housing

On arrival, the animals were separated and housed at random in polycarbonate cages (E-Type, Charles River, 255×405×197 mm) with stainless steel lids. Animals were housed in groups of five animals per cage according to their sex, in animal rooms with controlled temperature (22±2° C.), lighting (12/12 hours light/darkness), air pressure, number of air renovations and relative humidity (30-70%). The cages all had sawdust (Lignocel 3-4; Harlan Interfauna *Iberica*, Spain) on the floor as litter. All mice had free access to a dry, pelleted standard rodent diet (Teklad Global 2014; Harlan Interfauna *Iberica*, Spain). Water was provided ad libitum in bottles. Tap water supply to the animal rooms is periodically analysed to check its composition and to detect possible contaminants (chemical and microbiological).

Equipment and Materials
Equipment:
Animal balance Sartorius Mod. BP 2100
Surgical dissection equipment
Eppendorf 5415 C centrifuge
Nikon Eclipse E600FN microscope
Hook & Tucker instruments rotamixer
IKA Ultra Turrax Homogeniser
Sartorius Mod. BP 221S analytical balance
Materials and Reagents:
Sterile disposable syringes (1 ml)
Sterile Butterfly 25 G infusion set
Anaesthetic (Ketamine/Xylazine)
Topical Anaesthetic cream (EMLA, Astra Zeneca)
Dextran Sodium Sulphate 30.000-50.000 Da (MP Biomedicals)
Phosphate Buffered Saline (PBS; Sigma)
Neutral Buffered Formalin (VWR)
Experimental Protocol Study design: animals were divided into 5 experimental groups. Each group consisted of 10 males: Group A: Treated with Control vehicle (PBS) p.o. twice daily. Group B: Treated with methylprednisolone (1 mg/kg p.o. twice daily). Group C: Treated with hBD2 (0.05 mg/kg p.o. twice daily). Group D: Treated with hBD2 (0.5 mg/kg p.o. daily). Group E: Treated with hBD2 (5 mg/kg p.o. daily). Animal allocation to all experimental groups was done in a randomized manner. A maximum of 5 mice were housed in each cage (as per Directive 86/609/EEC). All animals were weighed on their arrival at the laboratory and prior to the administration of the test items.

Administration of the Test Substance

The control vehicle and hBD2 were administered orally with the use of a sterile cannula in a dosing volume of 10 ml/kg body weith. The animals of all groups received 2 doses daily (at 9.00 h and 17.00 h) of the corresponding test item (test, reference or vehicle) for 10 consecutive days (experimental days 1-10).

Experimental Procedure
Induction of Colitis

Colitis was induced in mice by supplementing their drinking water with DSS 2% for 7 days. On Day 1 all mice were weighed and marked according to their experimental groups. The drinking bottle of each cage was filled with the DSS solution, making sure all bottle lids were mounted properly and that none were congested. On Day 3 any remaining solution in the bottles was emptied and refilled with fresh DSS solution. This procedure was repeated again on Day 5. On Day 8 any remaining solution was discarded and replaced with autoclaved water. Animals were sacrificed 2 days later on Day 10.

Clinical Assessment (Disease Activity Index)

Daily clinical assessment of DSS-treated animals was carried out, with the calculation of a validated clinical Disease Activity Index (DAI) ranging from 0 to 4 according to the following parameters: stool consistency, presence or absence of rectal bleeding and weight loss:

| Description | Score |
|---|---|
| Change in Body Weight: | |
| <1% | 0 |
| 1-5% | 1 |
| >5-10% | 2 |
| >10-15% | 3 |
| >15% | 4 |
| Rectal Bleeding: | |
| Negative | 0 |
| Positive | 4 |
| Stool Consistency: | |
| Normal | 0 |
| Loose Stools | 2 |
| Diarrhoea | 4 |

Bodyweight loss was calculated as the percent difference between the original bodyweight (Day 1) and the actual bodyweight on each experimental day (2-10). The appearance of diarrhoea is defined as mucus/faecal material adherent to anal fur. Rectal bleeding is defined as diarrhoea containing visible blood/mucus or gross rectal bleeding. The maximum score of the DAI each day is 12.

Euthanasia and Collection of Colon Samples

On day 10, two hours after the last administration of control vehicle, hBD2 or prednisolone, the animals were killed by an overdose of anaesthetic. Their colons were removed and their length and weight measured after exclusion of the caecum. Two sections (proximal and distal) of colon were taken from each animal and preserved in neutral buffered formalin for subsequent histological analysis (haematoxylin and eosin staining) according to the following scoring system:

Description Score: No changes observed (0). Minimal scattered mucosal inflammatory cell infiltrates, with or without minimal epithelial hyperplasia (1). Mild scattered to diffuse inflammatory cell infiltrates, sometimes extending into the submucosa and associated with erosions, with minimal to mild epithelial hyperplasia and minimal to mild mucin depletion from goblet cells (2). Mild to moderate inflammatory cell infiltrates that were sometimes transmural, often associated with ulceration, with moderate epithelial hyperplasia and mucin depletion (3). Marked inflammatory cell infiltrates that were often transmural and associated with ulceration, with marked epithelial hyperplasia and mucin depletion (4). Marked transmural inflammation with severe ulceration and loss of intestinal glands (5).

Histological Evaluation

Two sections (proximal and distal) of colon were taken from each animal, processed for histological analysis (haematoxylin and eosin staining) and scored by a blind observer according to the histological scoring system described above.

Statistical Analysis

The statistical significance of the results was evaluated using the statistics program GraphPad Instat 3. Results are expressed as the mean±standard error of the mean, where (n) is the number of animals. The difference between groups for body weight, colon weight and colon length was evaluated by Analysis of Variance (ANOVA) for unpaired data plus post-test Dunnett to allow for multiple comparisons. The difference between groups for disease activity index and histological score was evaluated by Kruskal-Wallis test for unpaired data+post-test of Dunn for multiple comparisons. A value of $P<0.05$ was taken as significant. In the figures and tables, significant differences versus the corresponding control (vehicle) group are denoted as: *P<0.05, P<0.01, *P<0.001.

Figure 1:
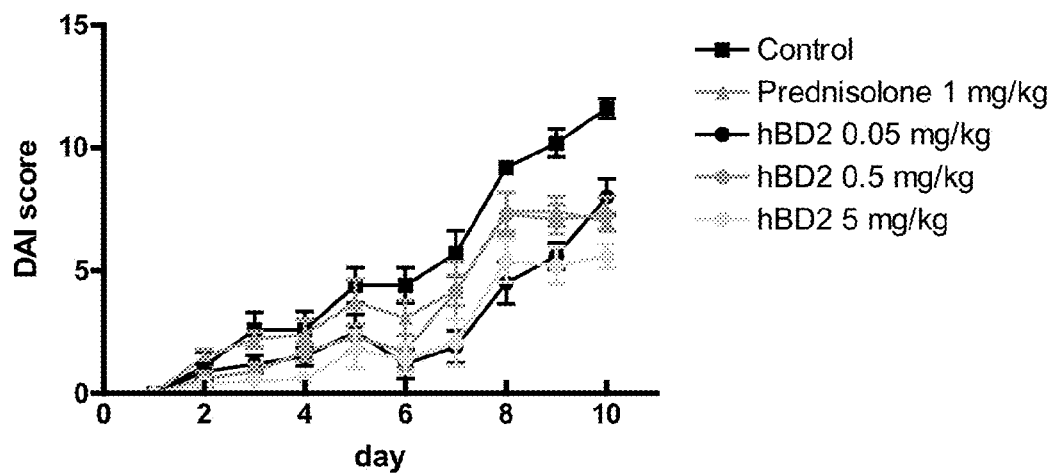
FIG. 1. Disease Activity Index (DAI) score (with body weight) progression during the study. Results are shown as the mean±the standard error of the mean for n=10 animals per group. Significant differences from control (vehicle)

Results In the present study, treatment with the test item NZ39000 (hBD2) resulted in a significant inhibition of the disease activity index (DAI) when administered daily, at three dose levels (0.05, 0.5, 5 mg/kg) via the oral route (FIG. 1 and tables below). A significant inhibition was observed after treatment with both the reference item (prednisolone) and with hBD2 with the following significant differences:

Days or treatments not mentioned was not significant different.

| hBD2 0.05 mg/kg | | | |
|---|---|---|---|
| Day | NZ39000 DAI | Vehicle DAI | Statistical significance vs. vehicle |
| 6 | 1.2 ± 0.59 | 4.4 ± 0.72 | P < 0.01 |
| 7 | 1.9 ± 0.66 | 5.7 ± 0.92 | P < 0.05 |
| 8 | 4.5 ± 0.86 | 9.2 ± 0.25 | P < 0.001 |
| 9 | 5.6 ± 0.54 | 10.2 ± 0.57 | P < 0.001 |
| 10 | 8 ± 0.73 | 11.6 ± 0.4 | P < 0.05 |

| hBD2 0.5 mg/kg | | | |
|---|---|---|---|
| Day | NZ39000 DAI | Vehicle DAI | Statistical significance vs. vehicle |
| 6 | 1.7 ± 0.67 | 4.4 ± 0.72 | P < 0.05 |
| 9 | 7.1 ± 0.61 | 10.2 ± 0.57 | P < 0.05 |
| 10 | 7.3 ± 0.7 | 11.6 ± 0.4 | P < 0.01 |

| hBD2 5 mg/kg | | | |
|---|---|---|---|
| Day | NZ39000 DAI | Vehicle DAI | Statistical significance vs. vehicle |
| 3 | 0.5 ± 0.27 | 2.6 ± 0.7 | P < 0.05 |
| 4 | 0.6 ± 0.27 | 2.6 ± 0.75 | P < 0.05 |
| 5 | 1.8 ± 0.76 | 4.4 ± 0.72 | P < 0.05 |
| 6 | 1.4 ± 0.6 | 4.4 ± 0.72 | P < 0.05 |
| 7 | 2.1 ± 0.96 | 5.7 ± 0.92 | P < 0.05 |
| 8 | 5.4 ± 0.87 | 9.2 ± 0.25 | P < 0.01 |
| 9 | 5.2 ± 0.76 | 10.2 ± 0.57 | P < 0.001 |
| 10 | 5.6 ± 0.48 | 11.6 ± 0.4 | P < 0.001 |

| Prednisolone 1 mg/kg | | | |
|---|---|---|---|
| Day | Pred. DAI | Vehicle DAI | Statistical significance vs. vehicle |
| 6 | 7 ± 0.33 | 11.6 ± 0.4 | P < 0.01 |

A significant reduction was also observed for the both proximal and distal colon (FIGS. 2 and 3).

Conclusions

The results demonstrate that orally administered hBD2 at the tested doses significantly reduces the increase in Disease Activity Index induced by DSS administration at day 6, 7, 8, 9, and 10 for 0.05 mg/kg, at day 6, 9 and 10 for 0.5 mg/kg and at day 3, 4, 5, 6, 7, 8, 9 and 10 at 5 mg/kg. Similarly to the results obtained with the Disease Activity Index, histological analysis of the proximal and distal colons of each animal on day 10 revealed a very significant reduction of histological damage score by orally administered hBD2. The effect was more pronounced in the proximal than the distal colons. In the present study, treatment with the test item hBD2 resulted in a significant inhibition of the disease activity index (DAI) when administered daily, at 3 dose levels by the oral route. The reference item (Prednisolone) is known to have a significant appetite suppressant effect in mice (and it was administered twice each day), which can in turn result in a significant effect over animal body weight unrelated to the severity of the disease. To take this effect into consideration, an additional DAI score was also carried out without the change in body weight effect, only stool consistency and rectal bleeding were used as measurable parameters. In this case the test item hBD2 also demonstrated a very significant anti-inflammatory activity, as did the reference item prednisolone. Administration of dextran sodium sulphate resulted in a significant inflammation and injury of the animals' colonic tissue, as evidenced after histological examination. This injury was more pronounced in the distal section of the colon when compared with the proximal section. Treatment with the test item hBD2 twice daily, at 3 dose levels, resulted in a significant reduction of this histological damage in the proximal colon. Similarly, treatment with the test item hBD2 twice daily, at the intermediate and high dose levels, also resulted in a significant reduction of the histological damage in the distal colon. Treatment with prednisolone at a dose of 1 mg/kg p.o. twice daily (Group B) also significantly reduced the histological injury induced by DSS in the proximal and the distal colon. The results also show a significant increase in body weight in the animals treated with the high dose of the test item on day 10 (P<0.05) when compared to the control group. This result would suggest an improvement in the animals' general health status in the test item groups mentioned leading to less loss of body weight (for example by eating more, less diarrhea, etc). The animals treated with prednisolone (group B) show a significant decrease in body weight from day 2 until the end of the study. As mentioned previously, this decrease in body weight cannot be taken as an indication of general health status of the animals in this particular case, as prednisolone is known to have a significant inhibitory effect over appetite in mice, which would explain the decrease in body weight. The results obtained in the present study demonstrate an anti-inflammatory activity of orally administered hBD2 in the model of DSS colitis induced in the mouse after a 10-day treatment period.

The invention claimed is:

1. A method of reducing inflammation or injury in the colon, said method comprising oral administration of a therapeutically effective amount of a mammalian beta defensin to a subject, wherein said mammalian beta defensin is administered at least twice daily.

2. The method of claim 1, wherein the subject is human and the mammalian beta defensin is a human beta defensin.

3. The method of claim 1, wherein the mammalian beta defensin has at least 80% sequence identity to an amino acid sequence selected from the group consisting of SEQ ID NO: 1, SEQ ID NO: 2, SEQ ID NO: 3, and SEQ ID NO: 4.

4. The method of claim 1, wherein the mammalian beta defensin has at least 80% sequence identity to SEQ ID NO: 2.

5. The method of claim 1, wherein the mammalian beta defensin is a variant of human beta defensin 2, wherein no more than 10 amino acids have been changed, compared to SEQ ID NO: 2.

6. The method of claim 1, wherein the mammalian beta defensin has the amino acid sequence of SEQ ID NO: 2.

7. The method of claim 1, wherein said mammalian beta defensin is administered three or four times daily.

8. The method of claim 1, wherein the mammalian beta defensin is administered at a daily dosage of from about 0.0001-10 mg/kg.

9. The method of claim 1, wherein the colon is the distal colon or the proximal colon.

* * * * *

SEQUENCE LISTING

<160> NUMBER OF SEQ ID NOS: 9

<210> SEQ ID NO 1
<211> LENGTH: 36
<212> TYPE: PRT
<213> ORGANISM: Homo sapiens
<220> FEATURE:

<223> OTHER INFORMATION: mat_peptide

<400> SEQUENCE: 1

Asp His Tyr Asn Cys Val Ser Ser Gly Gly Gln Cys Leu Tyr Ser Ala
1               5                   10                  15

Cys Pro Ile Phe Thr Lys Ile Gln Gly Thr Cys Tyr Arg Gly Lys Ala
            20                  25                  30

Lys Cys Cys Lys
        35

<210> SEQ ID NO 2
<211> LENGTH: 41
<212> TYPE: PRT
<213> ORGANISM: Homo sapiens
<220> FEATURE:
<223> OTHER INFORMATION: mat_peptide

<400> SEQUENCE: 2

Gly Ile Gly Asp Pro Val Thr Cys Leu Lys Ser Gly Ala Ile Cys His
1               5                   10                  15

Pro Val Phe Cys Pro Arg Arg Tyr Lys Gln Ile Gly Thr Cys Gly Leu
            20                  25                  30

Pro Gly Thr Lys Cys Cys Lys Lys Pro
        35                  40

<210> SEQ ID NO 3
<211> LENGTH: 45
<212> TYPE: PRT
<213> ORGANISM: Homo sapiens
<220> FEATURE:
<223> OTHER INFORMATION: mat_peptide

<400> SEQUENCE: 3

Gly Ile Ile Asn Thr Leu Gln Lys Tyr Tyr Cys Arg Val Arg Gly Gly
1               5                   10                  15

Arg Cys Ala Val Leu Ser Cys Leu Pro Lys Glu Glu Gln Ile Gly Lys
            20                  25                  30

Cys Ser Thr Arg Gly Arg Lys Cys Cys Arg Arg Lys Lys
        35                  40                  45

<210> SEQ ID NO 4
<211> LENGTH: 50
<212> TYPE: PRT
<213> ORGANISM: Homo sapiens
<220> FEATURE:
<223> OTHER INFORMATION: mat_peptide

<400> SEQUENCE: 4

Glu Phe Glu Leu Asp Arg Ile Cys Gly Tyr Gly Thr Ala Arg Cys Arg
1               5                   10                  15

Lys Lys Cys Arg Ser Gln Glu Tyr Arg Ile Gly Arg Cys Pro Asn Thr
            20                  25                  30

Tyr Ala Cys Cys Leu Arg Lys Trp Asp Glu Ser Leu Leu Asn Arg Thr
            35                  40                  45

Lys Pro
    50

<210> SEQ ID NO 5
<211> LENGTH: 37
<212> TYPE: PRT
<213> ORGANISM: Homo sapiens
<220> FEATURE:

```
<223> OTHER INFORMATION: hBD-4 variant consisting of amino acids 3-39 of
      SEQ ID NO: 4
<220> FEATURE:
<223> OTHER INFORMATION: mat_peptide

<400> SEQUENCE: 5

Glu Leu Asp Arg Ile Cys Gly Tyr Gly Thr Ala Arg Cys Arg Lys Lys
1               5                   10                  15

Cys Arg Ser Gln Glu Tyr Arg Ile Gly Arg Cys Pro Asn Thr Tyr Ala
            20                  25                  30

Cys Cys Leu Arg Lys
            35

<210> SEQ ID NO 6
<211> LENGTH: 40
<212> TYPE: PRT
<213> ORGANISM: Mus musculus
<220> FEATURE:
<223> OTHER INFORMATION: mat_peptide

<400> SEQUENCE: 6

Lys Ile Asn Asn Pro Val Ser Cys Leu Arg Lys Gly Gly Arg Cys Trp
1               5                   10                  15

Asn Arg Cys Ile Gly Asn Thr Arg Gln Ile Gly Ser Cys Gly Val Pro
            20                  25                  30

Phe Leu Lys Cys Cys Lys Arg Lys
            35                  40

<210> SEQ ID NO 7
<211> LENGTH: 41
<212> TYPE: PRT
<213> ORGANISM: Macaca mulatta

<400> SEQUENCE: 7

Gly Ile Gly Asp Pro Val Thr Cys Leu Lys Asn Gly Ala Ile Cys His
1               5                   10                  15

Pro Val Phe Cys Pro Arg Arg Tyr Lys Gln Ile Gly Thr Cys Gly Leu
            20                  25                  30

Pro Gly Thr Lys Cys Cys Lys Lys Pro
            35                  40

<210> SEQ ID NO 8
<211> LENGTH: 41
<212> TYPE: PRT
<213> ORGANISM: Pan troglodytes

<400> SEQUENCE: 8

Gly Ile Ser Asp Pro Val Thr Cys Leu Lys Ser Gly Ala Ile Cys His
1               5                   10                  15

Pro Val Phe Cys Pro Arg Arg Tyr Lys Gln Ile Gly Thr Cys Gly Leu
            20                  25                  30

Pro Gly Thr Lys Cys Cys Lys Lys Pro
            35                  40

<210> SEQ ID NO 9
<211> LENGTH: 44
<212> TYPE: PRT
<213> ORGANISM: Pongo abelii

<400> SEQUENCE: 9

Val Phe Gly Asp Ile Ser Asn Pro Val Thr Cys Leu Arg Ser Gly Ala
1               5                   10                  15
```

-continued

```
Ile Cys His Pro Gly Phe Cys Pro Arg Arg Tyr Lys His Ile Gly Thr
            20                  25                  30

Cys Gly Leu Ser Val Ile Lys Cys Cys Lys Lys Pro
            35                  40
```